(12) United States Patent
West et al.

(10) Patent No.: US 10,617,896 B1
(45) Date of Patent: Apr. 14, 2020

(54) DEVICE TO PREVENT HYPOTHERMIA AND INCREASE COLD-WEATHER SURVIVAL, UTILIZING THE USER'S EXHALED AIR

(71) Applicants: Stephen Gary West, Hillsborough, NC (US); Ronald Bussetti, Raleigh, NC (US)

(72) Inventors: Stephen Gary West, Hillsborough, NC (US); Ronald Bussetti, Raleigh, NC (US)

( * ) Notice: Subject to any disclaimer, the term of this patent is extended or adjusted under 35 U.S.C. 154(b) by 0 days.

(21) Appl. No.: 16/557,402

(22) Filed: Aug. 30, 2019

Related U.S. Application Data

(60) Provisional application No. 62/820,981, filed on Mar. 20, 2019.

(51) Int. Cl.
| | |
|---|---|
| *A62B 33/00* | (2006.01) |
| *A62B 9/02* | (2006.01) |
| *A62B 7/12* | (2006.01) |
| *A61F 7/00* | (2006.01) |
| *A62B 9/06* | (2006.01) |

(52) U.S. Cl.
CPC ............... *A62B 33/00* (2013.01); *A62B 7/12* (2013.01); *A62B 9/02* (2013.01); *A61F 7/00* (2013.01); *A61F 2007/0061* (2013.01); *A62B 9/06* (2013.01)

(58) Field of Classification Search
CPC .............. A62B 33/00; A62B 9/02; A62B 7/12
See application file for complete search history.

(56) References Cited

U.S. PATENT DOCUMENTS

| 1,880,998 | A | * | 10/1932 | Sturtevant | ................ | A62B 9/06 |
| | | | | | | 128/207.16 |
| 5,490,501 | A | * | 2/1996 | Crowley | ................ | A62B 33/00 |
| | | | | | | 128/200.24 |
| 2010/0186745 | A1 | * | 7/2010 | Mashak | ................ | A61M 16/00 |
| | | | | | | 128/204.26 |

FOREIGN PATENT DOCUMENTS

| FR | 1443927 A | * | 7/1966 | ............ | A61M 16/00 |
| WO | WO-2018220590 A1 | * | 12/2018 | ............ | A61M 16/00 |

\* cited by examiner

*Primary Examiner* — Bradley H Philips

(57) ABSTRACT

A hypothermia-prevention device is provided. The hypothermia-prevention device provides a three-port valve system having an inhalation port, a respiration port and an exhalation port, respectively wherein an in-take valve fluidly connects the inhale port to the respiration port and wherein an out-take valve fluidly connects the exhale port to the respiration port. The out-take and in-take valves are adapted to respond to the negative and positive pressure urged by way respiration of a user through the respiration port so that the exhale air is directed through the exhale port while colder inhale air is excluded through the exhalation port. The exhale port provides an out-tube for selectively directing the warmer exhale air to necessary body parts of the user.

10 Claims, 4 Drawing Sheets

DEVICE TO PREVENT HYPOTHERMIA AND INCREASE COLD-WEATHER SURVIVAL, UTILIZING THE USER'S EXHALED AIR

CROSS-REFERENCE TO RELATED APPLICATION

This application claims the benefit of priority of U.S. provisional application No. 62/820,981, filed 20 Mar. 2019, the contents of which are herein incorporated by reference.

BACKGROUND OF THE INVENTION

The present invention relates to medical and emergency devices and, more particularly, to a device to prevent hypothermia and increase cold-weather survival, utilizing the user's exhaled air.

Significant loss of heat from an individual's body causes hypothermia, which can be fatal in cold-weather environments.

There is a need for a device to prevent hypothermia and increase cold-weather survival. The present invention is adapted to use heat normally lost during respiration to selectively warm the core area. The present invention embodies a three-port valve system, wherein two ports have check valves adapted to direct inhaled air to the mouth, and then direct exhaled warm air from the third port into tubing for selectively directing such warm air to the user's abdomen.

SUMMARY OF THE INVENTION

In one aspect of the present invention, the hypothermia-prevention device includes the following: a three-port valve system having an inhalation port, an exhalation port and a respiration port; an in-valve located between the inhalation port and the respiration port, the in-valve movable between an open-inhale condition and a closed-exhale condition fluidly disconnecting the inhalation port and the respiration port, wherein the in-valve is configured to move to the open-inhale condition upon a negative pressure urged at the respiration port; an out-valve located between the exhalation port and the respiration port, the out-valve movable between an open-exhale condition and a closed-inhale condition fluidly disconnecting the exhalation port and the respiration port, wherein the out-valve is configured to move to the open-exhale condition upon a positive pressure urged at the respiration port; and wherein the in-valve and the out-valve are biased in the closed-exhale condition and the closed-inhale condition, respectively, wherein the exhalation port comprises an out-tube depending therefrom; and further comprising at least one hole provided at the end of the out-tube.

In another aspect of the present invention, a hypothermia-prevention device includes the following: a three-way valve system having an inhalation port, an exhalation port and a respiration port; an in-valve located between the inhalation port and the respiration port, the in-valve movable between an open-inhale condition and a closed-exhale condition fluidly disconnecting the inhalation port and the respiration port, wherein the in-valve is configured to move to the open-inhale condition upon a negative pressure urged at the respiration port; an out-valve located between the exhalation port and the respiration port, the out-valve movable between an open-exhale condition and a closed-inhale condition fluidly disconnecting the exhalation port and the respiration port, wherein the out-valve is configured to move to the open-exhale condition upon a positive pressure urged at the respiration port, wherein the out-valve pivots away from the respiration port in the open-exhale condition; wherein the in-valve and the out-valve are biased in the closed-exhale condition and the closed-inhale condition, respectively, in the absence of positive or negative pressure at the respiration port; a mouthpiece fluidly connected to the respiration port; and an out-tube fluidly connected to the exhalation port.

In yet another aspect of the present invention, a method of utilizing exhaled air to prevent hypothermia includes the following: providing the above-mentioned hypothermia-prevention device; placing a distal end of the out-tube beneath an article of clothing of a human wearer; and the human wearer breathing through the mouthpiece.

These and other features, aspects and advantages of the present invention will become better understood with reference to the following drawings, description and claims.

DETAILED DESCRIPTION OF THE INVENTION

Figure 1:
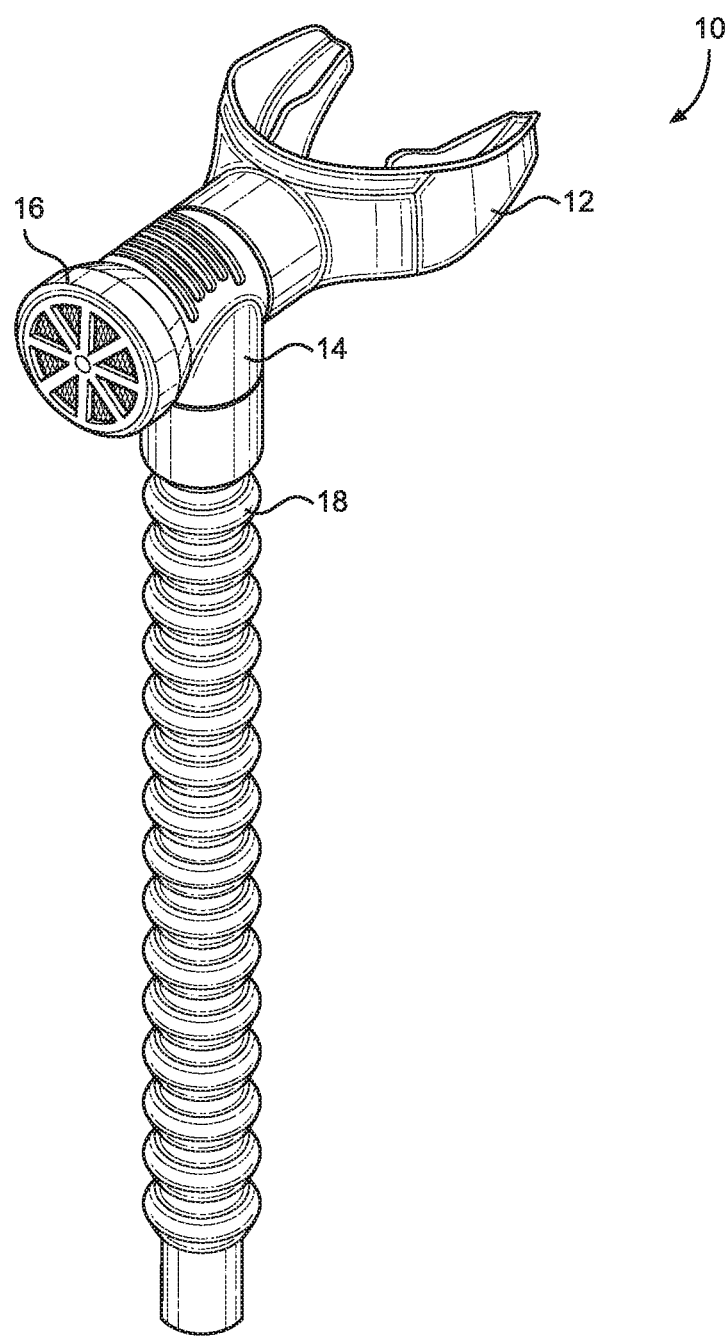
FIG. 1 is a perspective view of an exemplary embodiment of the present invention.
Figure 2:
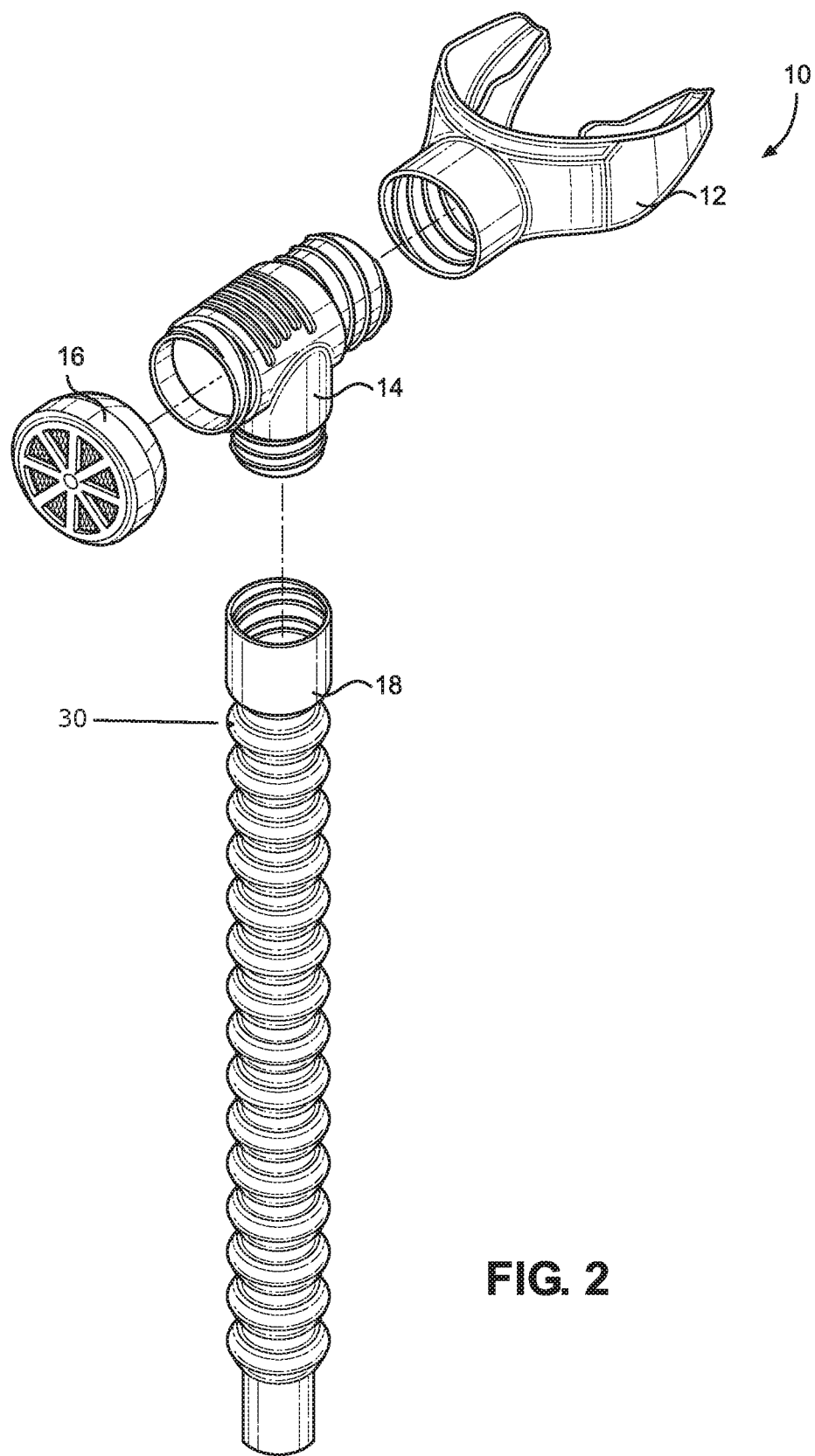
FIG. 2 is an exploded view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a hypothermia-prevention device embodied in a three-port valve system having an inhale port, a respiration port and an exhale port, wherein an in-take valve fluidly connects the inhalation port to the respiration port and wherein an out-take valve fluidly connects the exhalation port to the respiration port. The out-take and in-take valves are adapted to respond to the negative and positive pressure urged by way of a user's respiration through the respiration port so that exhale air is directed through the exhalation port while colder inhale air is excluded through the exhale port. The exhale port provides an out-tube for selectively directing the warmer exhale air to necessary body parts of the user.

Referring to FIGS. 1 through 4, the present invention may include a hypothermia-prevention device 10 to prevent hypothermia and increase cold-weather survival, and a method of using the same. The hypothermia-prevention device 10 may include a respiration port/mouthpiece 12 fluidly connected to an inhalation/intake port housing 16. Interconnecting the respiration port 12 and the inhalation port housing 16 may be a middle segment 14 fluidly connected to an exhalation port/out-tube 18 that depends from the middle segment 14, as illustrated in the FIGS.

Figure 3:
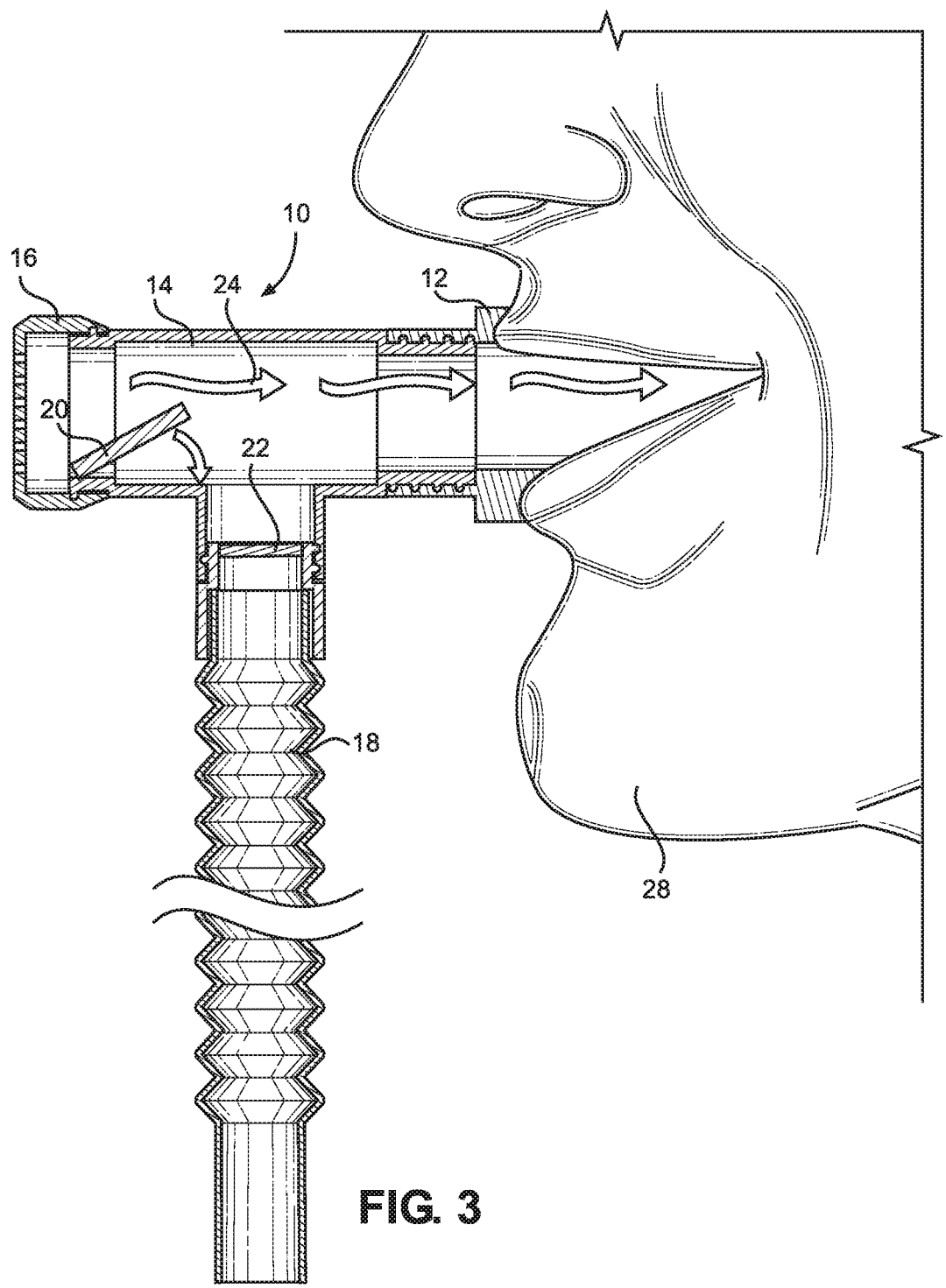
FIG. 3 is a diagrammatic view of an exemplary embodiment of the present invention, shown in use during inhalation.
Figure 4:
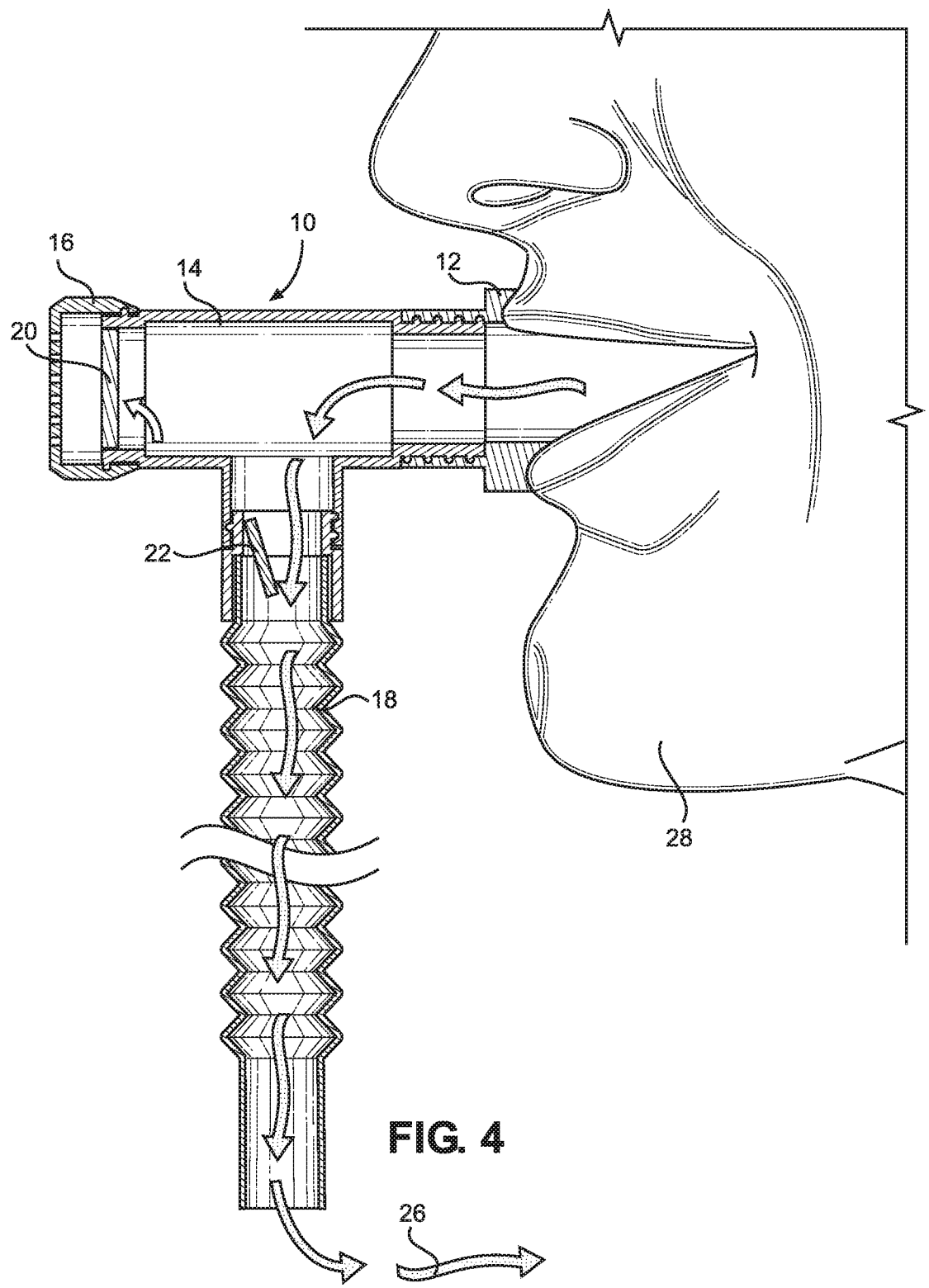
FIG. 4 is a diagrammatic view of an exemplary embodiment of the present invention, shown in use during exhalation.

As shown in FIGS. 3 and 4, the inhalation port housing 16 may provide an in-valve 20 at or near an inhalation interface of the inhalation port housing 16 and the middle segment 14, wherein the in-valve 20 is pivotably connected adjacent the inhalation interface so as to be moveable between a closed-exhale condition and an open-inhale condition. In the closed-exhale condition the fluid connection between the inhalation port housing 16 and the middle segment is closed off. The closed-exhale condition may be the biased condition of the in-valve 20 and/or results from the exhaling of user 28, as illustrated in FIG. 4. In the open-inhale condition, the in-valve 20 may pivot toward the respiration port 12 upon a change in air-pressure resulting from the user 28 inhaling, as illustrated in FIG. 3.

The middle segment 14 may provide an out-valve 22 at or near an exhalation interface with the out-tube 18. The middle segment 14 may be T-shaped, wherein the 'sole leg' of the T-shape is the exhalation port and connects directly to the out-tube 18. the out-valve 22 may be pivotably connected adjacent said out exhalation interface so as to be moveable between an open-exhale condition and a closed-inhale condition. In the closed-inhale condition the fluid connection between the middle segment 14 and the out-tube 18 is closed off. The closed-inhale condition may be the biased condition of the out-valve 22 and/or results from the difference in air pressure resulting from inhaling of the user 28, as illustrated in FIG. 3. In the open-exhale condition, the out-valve 22 may pivot away from the respiration port in the open-exhale condition upon the urging of a difference in air-pressure resulting from the user 28 exhaling, illustrated in FIG. 4.

It being understood that the in-valve 20 and the out-valve 22 may not necessarily physically pivot between different conditions to close off the associated fluid connections, but may nonetheless, through other mechanisms, close off said fluid connections in concert with the inhaling and exhaling of the user 28, as herein described and disclosed.

Accordingly, in certain embodiments, as the user 28 inhales, the in-valve 20 may be opened by negative pressure of inhalation. The open in-valve 20 then allows fresh, ambient "cold" air 24 into the mouthpiece 12, and then into the lungs. As the user 28 exhales into the respiration port/mouthpiece 12 the in-valve 20 is closed due to the increased air pressure produced during exhalation, so that warmed air does not escape through the inhalation/intake port housing 16. The exhaled "warmer" air 26 is thus directed through the out-valve 22 (which has opened due to the exhalation-induced increased air pressure) to the out-tube/conduit 18, and then selectively directed to other parts of the user's body or other individuals body (e.g., for rescue purposes), for example released into the abdominal area of the user 28. Additionally, the out-tube 18 and thus the warm air 26 may be operatively associated with an article of clothing or equipment that can trap the warm air 26 near a desired body part. The effect of the directed warm air 26 flow is that the selected area of the user 28 is efficiently warmed.

Generally speaking, the respiration port 12 is fluidly connected to the two check valves: the in-valve 20 and the out-valve 22 wherein the in-valve 20 opens under negative-pressure (inhalation), while the out-valve 22 opens under positive-pressure (exhalation) by way of the respiration port/mouthpiece 12. The out-valve 22 may be placed anywhere in the out-tube 18, rather than adjacent the respiration port/mouthpiece 12, or alternatively the out-valve 22 may be placed in a separate mouthpiece 12.

The materials used for the above apparatus includes, but are not limited to silicon, rubber, plastic or any other material appropriate for making tubing, including insulated tubing to conserve the exhale air's warmth. In addition, varying types of tubing may be used for the out-tube 18, such as collapsible, non-collapsible, differing widths and lengths, ribbed or smooth tubing. The mouthpiece 12 may be changed in shape or size, or may be eliminated altogether as, for instance, the user's mouth may merely be placed around the respiration port of the middle segment 14. This would require hand-holding the out-tube 18/middle segment 14 in place, as there may be no place for the teeth to hold onto the naked respiration port without eventually damaging it. In other words, the scuba-like mouthpiece 12 may be necessary for oral comfort as well as keeping the present invention in place hands-free.

In one embodiment, the present invention enables the delivery of slightly warmed air from the lungs during inhalation when the out-valve 22 is located in the out-tube 18. Holes 30 may be placed above the out-valve 22, for example in the out-tube 18, allowing some small amount of warmed, exhaled air that was forced into the abdominal area to flow into the mouthpiece 12 during inhalation, mixing with the fresh, cold air, in order to mitigate the cold temperature of the inhaled air entering the throat and lungs. This, however, may impede the efficiency of the entire system.

A method of using the present invention may include the following. The hypothermia-prevention device 10 disclosed above may be provided. When a user 28 is in a cold environment they would unpack the hypothermia-prevention device 10 from an appropriate carrying case. The user 28 may pull out (expand) the expandable out-tube 18 and place the distal end of the out-tube 18 within an inner layer or layers of clothing, ideally as close to the undergarments as possible. The user 28 would then place the respiration port/mouthpiece 12 in their mouth as they would as if snorkeling or scuba diving, breathing naturally through the mouthpiece 12. Fresh ambient cold air 24 would be inhaled through the exterior-accessed inhalation port in-valve 20 which is in the open position due to the negative pressure created by inhalation, while at the same time the lower positioned exhalation port export out-valve 22 is in the closed position due to the negative pressure. Upon exhalation, positive air pressure closes the in-valve 20 thus preventing the escape of the warmed exhaled air 26 through the inhalation/intake port 16. This same positive pressure opens the out-take valve 22 fluidly connected to or within the out-tube 18 resulting in the warm-air exhalation 26 to be directed therethrough and down the out-tube 18, enabling the warmer exhaled air 26 to be selectively directed toward the abdomen, the head, or other body parts in need of warmth. The resulting effect is an extremely efficient distribution of otherwise-lost body heat.

It should be understood, of course, that the foregoing relates to exemplary embodiments of the invention and that modifications may be made without departing from the spirit and scope of the invention as set forth in the following claims.

What is claimed is:
1. A hypothermia-prevention device, comprising:
a three-way valve system having an inhalation port, an exhalation port and a respiration port;
an in-valve located between the inhalation port and the respiration port, the in-valve movable between an open-inhale condition and a closed-exhale condition fluidly disconnecting the inhalation port and the respiration port, wherein the in-valve is configured to move to the open-inhale condition upon a negative pressure urged at the respiration port;

an out-valve located between the exhalation port and the respiration port, the out-valve movable between an open-exhale condition and a closed-inhale condition fluidly disconnecting the exhalation port and the respiration port, wherein the out-valve is configured to move to the open-exhale condition upon a positive pressure urged at the respiration port;

an intake housing removably secured to the inhalation port;

the intake housing dimensioned so that a distal end thereof is spaced apart from the inhalation port by less than a diameter of said inhalation port; and wherein the in-valve and the out-valve are biased in the closed-exhale condition and the closed-inhale condition, respectively.

2. The hypothermia-prevention device of claim 1, wherein in the absence of positive or negative pressure at the respiration port, the in-valve and the out-valve are biased in the closed-exhale condition and the closed-inhale condition, respectively.

3. The hypothermia-prevention device of claim 1, further comprising a mouthpiece fluidly connected to the respiration port.

4. The hypothermia-prevention device of claim 1, further comprising an out-tube fluidly connected to the exhalation port.

5. The hypothermia-prevention device of claim 1, wherein the in-valve pivots toward the respiration port in the open-inhale condition.

6. The hypothermia-prevention device of claim 1, wherein the out-valve pivots away from the respiration port in the open-exhale condition.

7. The hypothermia-prevention device of claim 1, wherein the exhalation port comprises an out-tube depending therefrom; and further comprising at least one hole (30) provided in the out-tube.

8. A hypothermia-prevention device, comprising:
a three-way valve system having an inhalation port, an exhalation port and a respiration port;
an in-valve located between the inhalation port and the respiration port, the in-valve movable between an open-inhale condition and a closed-exhale condition fluidly disconnecting the inhalation port and the respiration port, wherein the in-valve is configured to move to the open-inhale condition upon a negative pressure urged at the respiration port;
an out-valve located between the exhalation port and the respiration port, the out-valve movable between an open-exhale condition and a closed-inhale condition fluidly disconnecting the exhalation port and the respiration port, wherein the out-valve is configured to move to the open-exhale condition upon a positive pressure urged at the respiration port, wherein the out-valve pivots away from the respiration port in the open-exhale condition;
wherein the in-valve and the out-valve are biased in the closed-exhale condition and the closed-inhale condition, respectively, in the absence of positive or negative pressure at the respiration port;
a mouthpiece fluidly connected to the respiration port;
an intake housing removably secured to the inhalation port;
the intake housing dimensioned so that a distal end thereof is spaced apart from the inhalation port by less than a diameter of said inhalation port; and
an out-tube fluidly connected to the exhalation port.

9. A method of utilizing exhaled air to prevent hypothermia, comprising:
providing the hypothermia-prevention device of claim 8;
placing a distal end of the out-tube under an article of clothing of a human wearer; and
the human wearer breathing through the mouthpiece.

10. The hypothermia-prevention device of claim 4, wherein the device is structured so that dead space is minimized.

* * * * *